(12) United States Patent
Haltseu et al.

(10) Patent No.: US 10,912,662 B2
(45) Date of Patent: Feb. 9, 2021

(54) ELECTRICALLY DRIVEN ARTIFICIAL ARM AND METHOD OF USE

(71) Applicant: Bionicarm Ltd., Rishon Lezion (IL)

(72) Inventors: Aleh Haltseu, Rishon Lezion (IL);
Siarhei Arefyeu, Rishon Lezion (IL);
Illia Darashenka, Rishon Lezion (IL);
Viktar Farber, Rishon Lezion (IL)

(73) Assignee: BIONICARM LTD., Rishon Lezion (IL)

( * ) Notice: Subject to any disclaimer, the term of this patent is extended or adjusted under 35 U.S.C. 154(b) by 141 days.

(21) Appl. No.: 16/149,551

(22) Filed: Oct. 2, 2018

(65) Prior Publication Data
US 2019/0388248 A1 Dec. 26, 2019

(30) Foreign Application Priority Data
Jun. 21, 2018 (CA) ...................................... 3009219

(51) Int. Cl.
*A61F 2/70* (2006.01)
*A61F 2/54* (2006.01)
(Continued)

(52) U.S. Cl.
CPC ................ *A61F 2/70* (2013.01); *A61F 2/586* (2013.01); *A61F 2/7812* (2013.01);
(Continued)

(58) Field of Classification Search
CPC ...... A61F 2/54; A61F 2/58; A61F 2/70; A61F 2002/543; A61F 2002/586
(Continued)

(56) References Cited

U.S. PATENT DOCUMENTS

| 3,820,168 A | 6/1974 | Horvath |
| 5,413,611 A | 5/1995 | Haslam, II et al. |

(Continued)

FOREIGN PATENT DOCUMENTS

| AT | 273362 | 8/1969 |
| CN | 201920939 | 8/2011 |

(Continued)

OTHER PUBLICATIONS

International Search Report and Written Opinion issued in PCT/IB2019/054779, dated Sep. 27, 2019.
(Continued)

*Primary Examiner* — Bruce E Snow
(74) *Attorney, Agent, or Firm* — Hamre, Schumann, Mueller & Larson, P.C.

(57) ABSTRACT

Disclosed is a prosthesis for a person with an amputation below the elbow to provide a replacement for at least a lower arm of the person. The prosthesis includes a receiving sleeve adapted to be attached to a stump of the person such that the stump can move the receiving sleeve. An electromechanical hand is attached to the receiving sleeve, the electromechanical hand having a rotary mechanism, a control unit, at least one finger and at least one motor. The rotary mechanism includes a potentiometer having a shaft in communication with the receiving sleeve such that a displacement of the receiving sleeve causes a corresponding rotation of the shaft of the potentiometer. The control unit is configured to measure the corresponding rotation of the shaft of the potentiometer and send a signal to the at least one motor to actuate the at least one finger.

14 Claims, 4 Drawing Sheets

(51) Int. Cl.
*A61F 2/78* (2006.01)
*A61F 2/58* (2006.01)

(52) U.S. Cl.
CPC ... *A61F 2002/587* (2013.01); *A61F 2002/701* (2013.01); *A61F 2002/7837* (2013.01)

(58) Field of Classification Search
USPC ..................................................... 623/57–64
See application file for complete search history.

(56) References Cited

U.S. PATENT DOCUMENTS

| | | | |
|---|---|---|---|
| 5,800,572 A * | 9/1998 | Loveall ................. | A61F 2/583 623/33 |
| 5,888,213 A * | 3/1999 | Sears ...................... | A61F 2/68 623/24 |
| 7,186,270 B2 | 3/2007 | Elkins | |
| 7,828,857 B2 | 11/2010 | Farnsworth et al. | |
| 8,821,587 B2 | 9/2014 | Lanier et al. | |
| 2004/0078091 A1 | 4/2004 | Elkins | |
| 2005/0234564 A1 | 10/2005 | Fink et al. | |
| 2008/0243265 A1 | 10/2008 | Lanier et al. | |
| 2016/0051383 A1 | 2/2016 | Goldfarb et al. | |
| 2019/0209345 A1* | 7/2019 | LaChappelle ............ | A61F 2/72 |

FOREIGN PATENT DOCUMENTS

| | | |
|---|---|---|
| EP | 2890333 | 12/2016 |
| RO | 92470 | 5/1987 |
| RU | 2506931 C2 | 2/2014 |
| SU | 1662548 * | 6/1988 |
| WO | 2011/021921 | 2/2011 |
| WO | 2014/033373 | 3/2014 |
| WO | 2014111843 A2 | 7/2014 |
| WO | 2015/170964 | 11/2015 |
| WO | 2016182421 A1 | 11/2016 |
| WO | 2016/202613 | 12/2016 |
| WO | 2017/062755 | 4/2017 |

OTHER PUBLICATIONS

"Input Sensors", Liberating Technologies, Inc., 2013, 5 pages, available at: http://www.liberatingtech.com/products/electronics/Input_Sensors.asp.

"Bebionic Hands", Liberating Technologies, Inc., 2013, 6 pages, available at: http://www.liberatingtech.com/products/hands/Bebionic_Hands.asp.

"Remote Controlled Operated Prosthetic Arm", a Thesis by Amardeep Bajwa, Thapar University, Jul. 2010, 59 pages (http://hdl.handle.net/10266/1181).

* cited by examiner

ELECTRICALLY DRIVEN ARTIFICIAL ARM AND METHOD OF USE

The present subject matter relates to a prosthesis for a person with a limb amputation, such as an arm amputation below the elbow, to provide a replacement for the hand and lower arm of such person.

Considerations concerning performance requirements of prosthetic apparatuses are exceedingly complex. Various attempts have been made to provide operable prostheses. In conventional artificial arms, a mechanical system is employed with cables connected between the prosthesis and another part of the user's body. The user operates the prosthesis by pulling the cable by using drastic movements of the portion of the body to which the cables are attached. The movements required to pull the cable are large and unnatural.

SUMMARY

The following summary is intended to introduce the reader to the more detailed description that follows, and not to define or limit the claimed subject matter.

According to a first aspect, the present subject matter relates to a prosthesis for a person with an arm amputation below the elbow to provide a replacement for at least a lower arm of the person, the prosthesis including:
- a receiving sleeve adapted to be attached to an arm stump of the person such that the stump can move the receiving sleeve;
- an electromechanical hand attached to the receiving sleeve, the electromechanical hand having a rotary mechanism, a control unit, at least one finger, and at least one motor; and
- wherein the rotary mechanism includes a potentiometer having a shaft in communication with the receiving sleeve such that a displacement of the receiving sleeve causes a corresponding rotation of the shaft of the potentiometer;
- wherein the control unit is configured to measure the corresponding rotation of the shaft of the potentiometer and send a signal to the at least one motor to actuate the at least one finger.

According to a second aspect, the present subject matter relates to a prosthesis for a person with an arm amputation below the elbow to provide a replacement for at least a lower arm of the person, the prosthesis including:
- a sleeve casing adapted to be attached to an arm stump of the person, the sleeve casing including a back portion and a forward portion, the back portion having a hollow cavity therewithin for receiving the stump;
- a rotatable receiving sleeve mounted within the hollow cavity, the receiving sleeve adapted to snuggly fit the stump such that the stump can move the receiving sleeve;
- an electromechanical hand attached to the forward portion of the sleeve casing, the electromechanical hand having a rotary mechanism, a control unit, at least one finger, and at least one motor; and
- wherein the rotary mechanism includes a potentiometer having a shaft in communication with the rotatable receiving sleeve such that a rotation of the receiving sleeve causes a corresponding rotation of the shaft of the potentiometer;
- wherein the control unit is configured to measure the corresponding rotation of the shaft of the potentiometer and send a signal to the at least one motor to actuate the at least one finger.

In some examples, the prosthesis further includes a battery pack module removably received within a receptacle in the prosthesis and connected to the control unit or the at least one motor for providing electrical power thereto.

In some examples, the prosthesis includes five fingers and a separate motor for each finger.

In some examples, the receiving sleeve is fixed to the shaft of the potentiometer.

In some examples, the prosthesis further includes a control switch for selecting different modes to capture and hold an object, the control switch being located on an external surface of the electromechanical hand and adapted to configure the control unit.

In some examples, the control switch is adapted to configure minimum and maximum values of the rotation of the receiving sleeve.

In some examples, the prosthesis further includes an internal memory unit for storing configuration data of the control unit.

According to a third aspect, the present subject matter relates to a method for setting operating conditions for a limb prosthesis, including:
- providing a limb prosthesis having a receiving sleeve;
- inserting a limb stump of a user into the receiving sleeve;
- rotating the receiving sleeve as far as possible to the right while a potentiometer connected to the receiving sleeve changes its value, such that when a rightmost position is reached, a rightmost potentiometer value is stored on an internal memory of the control unit of the prosthesis;
- rotating the receiving sleeve to the left, such that when a leftmost position is reached, a leftmost potentiometer value is recorded in the internal memory; and
- obtaining a range of numerical values between the rightmost and leftmost positions in which the user can rotate the receiving sleeve.

DRAWINGS

In order that the claimed subject matter may be more fully understood, reference will be made to the accompanying drawings, in which:

DESCRIPTION OF PARTICULAR EMBODIMENTS

Figure 1:
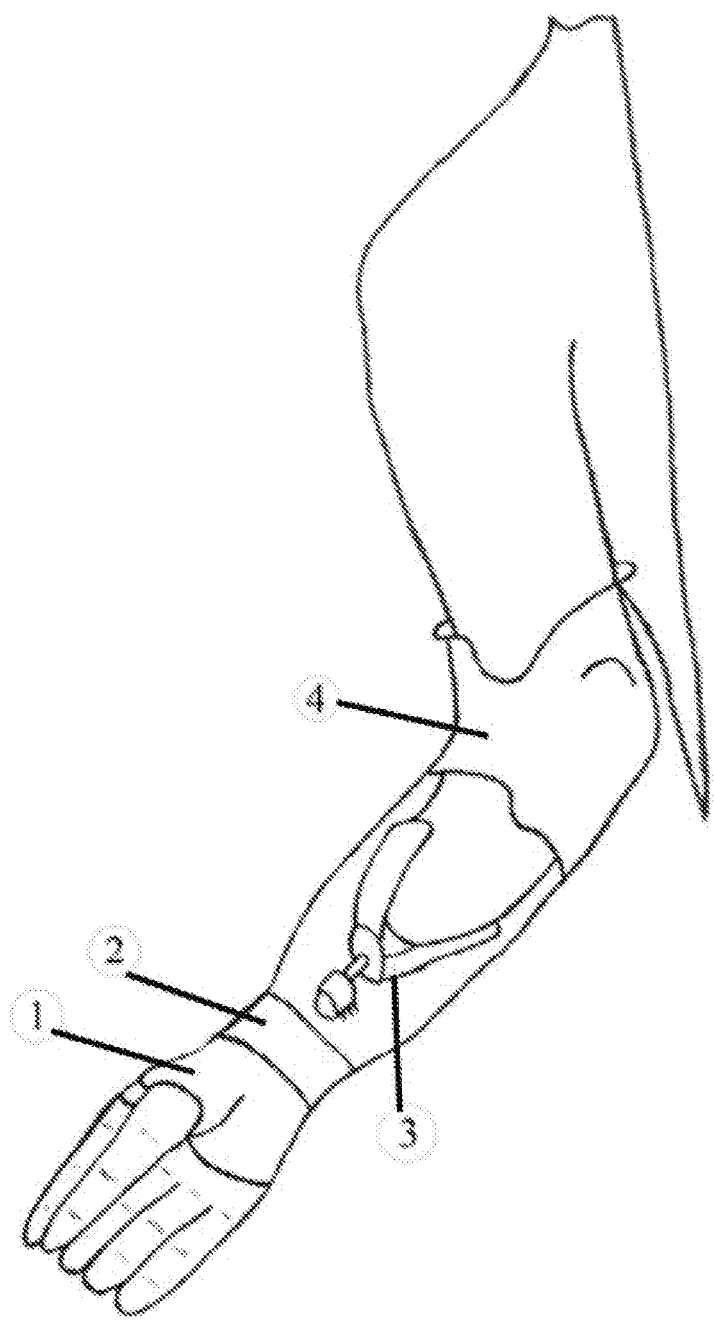
FIG. 1 is a perspective view of a lower arm prosthesis according to one example.

In the following description, specific details are set out to provide examples of the claimed subject matter. However, the embodiments described below are not intended to define or limit the claimed subject matter.

It will be appreciated that, for simplicity and clarity of illustration, where considered appropriate, reference numerals may be repeated among the figures to indicate corresponding or analogous elements or steps. Numerous specific details are set forth in order to provide a thorough understanding of the exemplary embodiments of the subject matter described herein. However, it will be understood by those of ordinary skill in the art that the embodiments described herein may be practiced without these specific details. In other instances, well-known methods, procedures and components have not been described in detail so as not to obscure the present subject matter. Furthermore, this description is not to be considered as limiting the scope of the subject matter in any way but rather as illustrating the various embodiments.

For example, there is provided a prosthesis for a person with an arm amputation below the elbow to provide a replacement for the hand and lower arm of the person. For example, the prosthesis includes a receiving sleeve adapted to be attached to an arm stump of the person such that the stump can move the receiving sleeve. For example, the prosthesis also includes an electromechanical hand attached to the receiving sleeve, the electromechanical hand having a rotary mechanism, a control unit, fingers and motors. The rotary mechanism includes a potentiometer having a shaft in communication with the receiving sleeve such that a displacement of the receiving sleeve causes a corresponding rotation of the shaft of the potentiometer. The control unit is configured to measure the corresponding rotation of the shaft of the potentiometer and send a signal to the at least one motor to actuate the at least one finger.

For example, the present subject matter provides the design of the forearm prosthesis and the method of controlling thereof, comprising an artificial electromechanical hand with a drive for each finger, a hand rotation mechanism, a supporting sleeve made as non-falling, connected to the support body and provided with fastening elements, a turnable receiving sleeve disposed in the supporting sleeve. The present subject matter is characterized in that the control element of the artificial hand is a potentiometer the axis of which is connected directly to the receiving sleeve. The potentiometer receives the current position of the patient's stump and sends a control signal to the electronic control unit. For example, the receiving sleeve may be made by 3D printing, which makes it possible to quickly customize the device. Fingers and their drive (except for the thumb) are made in one standard size, which makes them interchangeable. This fact significantly increases the maintainability of the entire prosthesis.

The artificial hand may contain a separate electric motor with a feedback on each finger. The individual finger drive with the feedback adds functionality to the artificial electromechanical hand. Different grips that are most suitable for performing some operations can be programmed. In addition, the individual drive of the fingers makes it possible to adapt to the various shapes of objects when grasping, thereby ensuring the most reliable gripping of the object. The grip allows the patient to take and hold such items as a pen, a needle, kitchen appliances (forks, spoons, knives, cups, plates, glasses, etc.). Also, the prosthesis makes it possible to perform a variety of everyday operations such as: pouring water into the cup, taking a briefcase or bag, pressing keys on the computer keyboard or the mouse.

The forearm prosthesis may be controlled by a control board and a sensor that provide communication between the signals from the patient's body and the drive of the fingers. The control signals are generated when the forearm stump is rotated. At this moment, the receiving sleeve rotates, which, in turn, rotates the axis of the potentiometer. The potentiometer changes its value, which leads to a misalignment of the original data. This value is sent to the electronic control unit. The difference in values is the control signal. The electronic control unit receives this value and sends a control signal to each of the five motors. The direction of rotation of each motor depends on the signal sent from the electronic control unit. The electronic control unit monitors that each motor reaches a proportional value with a control signal, depending on the operating mode. This control algorithm provides a logical interconnection of all components of the prosthesis, enables the individual adjustment of the control unit to the patient, as well as changing the operation modes of the artificial electromechanical hand, monitors the correct operation of each finger.

Figure 2:
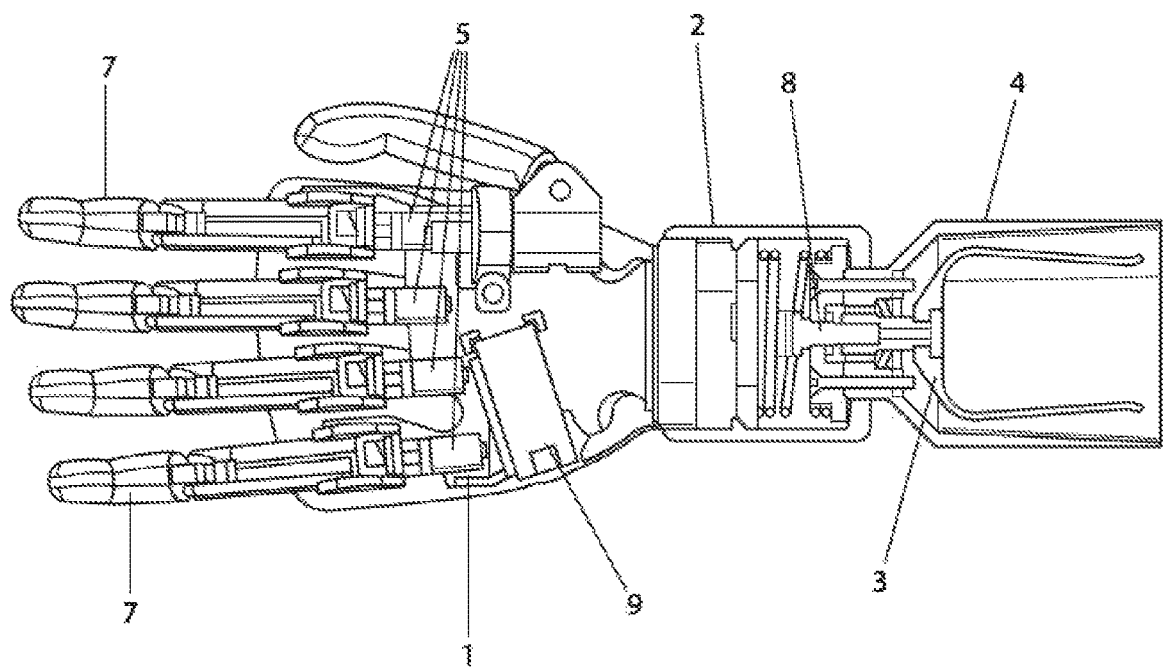
FIG. 2 is a cross section view of a hand prosthesis according to one example.
Figure 3:
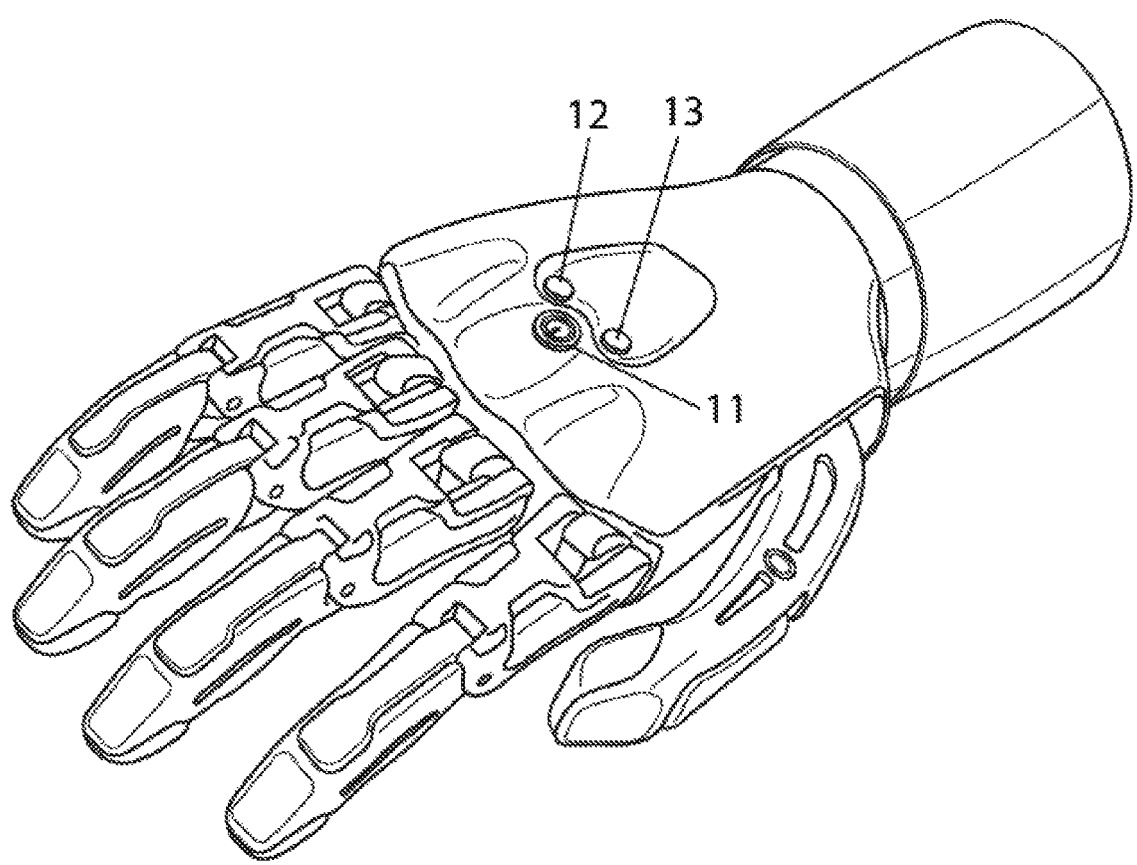
FIG. 3 is a top view of a hand prosthesis according to one example.

Embodiments of the prostheses as described herein are shown in FIGS. 1, 2 and 3. These prostheses can be used by a person with an amputation below the elbow. They provide a replacement for the hand and lower arm. Referring to FIGS. 1 and 2, the prosthesis has a sleeve casing 4 adapted to be attached to a stump area of the person. The sleeve casing has a back portion and a forward portion. The back portion has a hollow cavity therewithin for receiving the stump area. A receiving sleeve 3 can be mounted within the hollow cavity. For example, the receiving sleeve can be rotatable. The receiving sleeve can be adapted to snuggly fit the stump such that the stump can move the receiving sleeve.

Referring now to FIG. 2, an electromechanical hand 1 is attached to the forward portion of the sleeve casing 4. The electromechanical hand 1 has a rotary mechanism 2, a control unit 9, fingers 7 and motors 5.

Sensors provide communication between the signals from a patient's body and the drive of the fingers. An example of such sensors is a potentiometer. The potentiometer can be located inside the receiving sleeve. The receiving sleeve can be rotated by the stump, which rotates the shaft of the potentiometer. Moving the shaft of the potentiometer sends a control signal to the control unit, which in turn sends a control signal to each of the motors on the electromechanical hand for activating the fingers.

The prosthesis can be activated in several pre-selected modes to capture and hold an object. An example of a mode is the basic open-close mode. When this mode is selected, the prosthesis can be activated to be in an open state or in a closed state. The closed state, the prosthesis can hold an object, such as a ball or a glass of water. Another mode may allow the wearer to grasp a pen or pencil, or to make a pointing gesture. The different modes can be selected by a control switch on the sleeve or by means of a wireless controller.

Referring back to FIG. 2, inside the rotary mechanism 2, there is a potentiometer 8. The potentiometer 8 has a shaft in communication with the receiving sleeve 3 such that a rotation of the receiving sleeve 3 causes a corresponding rotation of the shaft of the potentiometer 8. The control unit is configured to measure the corresponding rotation of the shaft of the potentiometer. The control unit is also configured to send a signal to the motors to actuate their corresponding finger.

The present subject matter teaches a simple and reliable forearm prosthesis, which restores the basic functions of a natural hand, and also reduces the psychological tension of the disabled person. The movements of the fingers can be carried out from the control movement of the forearm stump. It is possible to rotate the hand and change the grips of the artificial hand. This is made possible by using a potentiometer that monitors the rotation of the receiving sleeve and sends a corresponding signal to the control unit. The control using can be configured to respond to various degrees of rotation of the receiving sleeve.

The prosthesis may include a battery pack module removably received within a receptacle in the prosthesis and connected to the control unit or the motors for providing electrical power thereto. The prosthesis can include five fingers and a separate motor for each finger. The receiving sleeve can be fixed to the shaft of the potentiometer. The prosthesis can include a control switch for selecting different modes to capture and hold an object. The control switch can be located on an external surface of the electromechanical hand and adapted to configure the control unit.

The control switch can be adapted to configure minimum and maximum values of the rotation of the receiving sleeve. The prosthesis can include an internal memory unit for storing configuration data of the control unit.

According to another aspect, there is disclosed a forearm prosthesis including an artificial electromechanical hand with a drive for each finger, a hand rotation mechanism, a supporting sleeve made non-falling, connected to the support body and provided with fastening elements, a turnable receiving sleeve disposed in the supporting sleeve. The present subject matter is characterized in that the control element of the artificial hand is a potentiometer the axis of which is connected directly to the receiving sleeve.

The potentiometer receives the current position of the patient's stump and sends a control signal to the electronic control unit. The forearm prosthesis is controlled by a control board and a sensor that provide communication between the signals from the patient's body and the drive of the fingers. The control signals are generated when the forearm stump is rotated. In response, the receiving sleeve rotates, which, in turn, rotates the shaft of the potentiometer.

The forearm prosthesis includes an electromechanical artificial hand with controlled drive, a control unit connected to a rotary mechanism and a supporting sleeve connected to the control unit. One of the main units of the prosthesis is an artificial hand. The main function of this unit is to perform various programmed grips and gestures.

Each finger is driven by an independent electric motor, which in turn is connected to the electronic control unit. The four fingers (index, middle, annulary and little) may be the same size. Due to this, they are interchangeable, which improves the maintainability of the entire prosthesis. The thumb rotates in two planes, which increases the possible number of grips that the hand is capable of.

The rotary mechanism is the link of the control unit and the hand. It also provides an opportunity to rotate the hand towards the sleeve. Rotating the hand increases the functionality of the prosthesis. Rotating the hand can be more convenient to adjust the grip to a certain action, for example, taking a cup or something from the table. For example, the angle of the hand rotation can reach 360 degrees.

The potentiometer can be directly connected to the electronic control unit. The shaft of the potentiometer can be rigidly connected to the receiving sleeve. The potentiometer changes its value when the receiving sleeve is rotated. It sends the current value to the electronic control unit located in the artificial hand.

The receiving sleeve is the unit that connects the human stump to the prosthesis. With the receiving sleeve, the patient controls the prosthesis, turning the stump inside the casing of the receiving sleeve.

The receiving sleeve and casing may be made individually according to the patient's stump, including, by 3D printing that provides an opportunity to make them in a timely manner. The receiving sleeve is fixed to the axis of the potentiometer. The casing provides the rigid connection of the prosthesis and the patient's supporting sleeve and allows the patient to rotate the receiving sleeve inside the supporting sleeve.

The supporting sleeve can be manufactured by a prosthetic physician individually for each patient. The supporting sleeve fixes and holds the prosthesis on the patient's arm and is structurally non-falling.

A method for setting operating conditions for a prosthesis is also provided herein. The method includes providing a prosthesis having a receiving sleeve and inserting a stump of a user into the receiving sleeve. Then, the method involves rotating the receiving sleeve as far as possible to the right while a potentiometer connected to the receiving sleeve changes its value, such that when a rightmost position is reached, a rightmost potentiometer value is stored on an internal memory of the control unit of the prosthesis. The method further includes rotating the receiving sleeve to the left, such that when a leftmost position is reached, a leftmost potentiometer value is recorded in the internal memory. The method includes obtaining a range of numerical values between the rightmost and leftmost positions in which the user can rotate the receiving sleeve.

For example, the minimum and maximum value of the rotation of the receiving sleeve can be initially set for the patient. For this, the patient inserts the stump into the receiving sleeve and rotates the receiving sleeve as far as possible to the right ("pronation"), while the potentiometer connected to the receiving sleeve changes its value. When the rightmost position is reached, the potentiometer value is stored in the internal memory of the electronic control unit. Then the patient turns the receiving sleeve to the maximum left ("supination"), while the potentiometer also changes its value. When the extreme left position is reached, the value from the potentiometer is also recorded in the internal memory of the electronic control unit. Thus, a range of numerical values in which the patient rotates the receiving sleeve is obtained. In addition, the electronic control unit stores information about the range of rotation values of the motor for each finger.

For example, an artificial hand can be controlled as follows. During the rotation of the forearm stump the receiving sleeve turns, followed by a rotation of the axis of the potentiometer. The potentiometer changes its value, which leads to a misalignment of the original data. This value is sent to the electronic control unit. The difference in values is the control signal. The electronic control unit receives this value and sends a control signal to each of the five electric motors. The direction of rotation of each motor depends on the signal sent from the control unit. The electronic control unit monitors that each motor reaches a proportional value with a control signal, depending on the operating mode.

Referring to FIG. 3, there is shown a control switch comprising buttons 11, 12 and 13 on a top surface of the prosthesis. The buttons can be used for controlling the operating mode of the prosthesis. Pressing and holding the button 11 for more than 2 seconds (pressing duration can be configured) turns the power on/off. A single press of the button 12 and keeping it pressed for less than 2 seconds (the duration can be configured) moves the hand to the next operating mode. Pressing the button 12 once and holding it for more than 5 seconds (the duration can be configured) stores in memory the maximum digital value of the control potentiometer. Pressing the button for 13 seconds and holding it for less than 2 seconds (the time can be configured) moves the hand to the previous operating mode, pressing the button 13 once and holding it for more than 5 seconds (the duration can be configured) stores in memory the minimum digital value of the control potentiometer.

Figure 4:
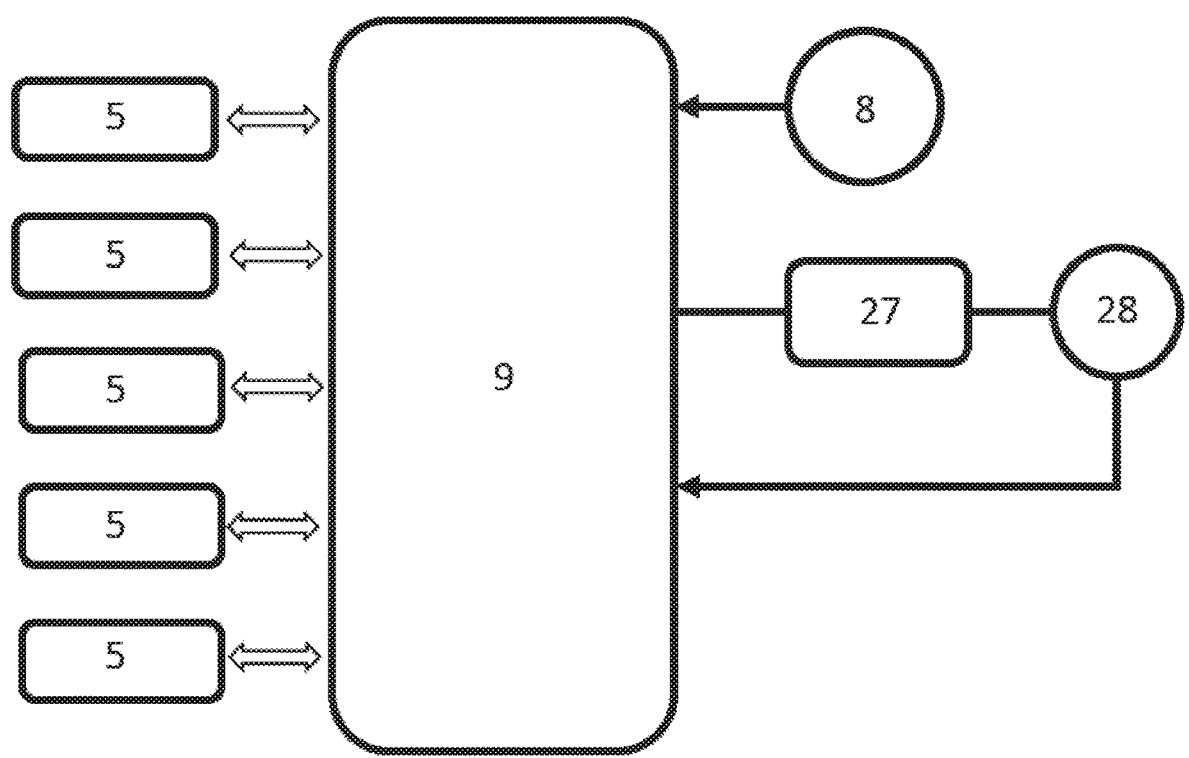
FIG. 4 illustrates a general diagram of the interaction between the electronic parts of a limb prosthesis according to one example.

Referring to FIG. 4, there is shown a control feedback system according to one embodiment. The control feedback system includes the control unit 9 connected to the potentiometer 8. The control unit 9 is connected to motors 5 with a feedback controller for each of the fingers. A rechargeable battery 27 is also connected to the control unit 9. A power button 28 is connected to both the rechargeable battery 27 and the control unit 9 to turn ON/OFF the rechargeable battery 27 and/or the control unit 9. Switch mode buttons 29 are also connected to the control unit 9.

In the prosthesis, a rechargeable internal LiPo battery (2S 7.4V) can be used to power all electric components. The electronic control unit (ECU) is connected to the each of the five motor controllers. The ECU reads the position of each finger (the ECU can activate or deactivate each motor). The ECU is connected to the potentiometer directly and reads values from the potentiometer to detect any changes. If the value of the potentiometer is changed, the ECU reacts depending of the program algorithm.

A program for controlling the prosthesis allows it to work as follows:

Customization

The initial adjustment of all parameters of the prosthesis occurs by connecting the prosthesis to the computer. The operator enters which modes and gestures are possible and determines the numerical values for these gestures and modes. The prosthesis is turned on/off by pressing button 1 (FIG. 3). When the prosthesis is turned on for the first time, all fingers always expand and contract maximally. Thus, when turning on, the range of values for each finger are initially set.

To adjust the minimum and maximum values of the turn of the receiving sleeve, the patient inserts the stump into the receiving sleeve and rotates it as far as possible to the right. The potentiometer connected to the receiving sleeve changes its value when turning. Then the patient presses button 12 in FIG. 3 (the button that is used for setting the maximum digital value of the potentiometer position) and holds it for a few seconds (the duration is configured). The electronic control unit reads the current digital value of the potentiometer and stores it in the internal memory of the electronic control unit as the maximum value. Then the patient turns the receiving sleeve as far to the left, while the potentiometer also changes its value. After that, the patient presses button 13 in FIG. 3 (the button that is used for setting the minimum digital value of the potentiometer position) and holds it for a few seconds (the duration is configured). The electronic control unit reads this value and stores it in the internal memory of the electronic control unit as the minimum value. Thus, the range of digital values in which the patient can rotate the receiving sleeve is set.

Basic Operating Mode

As an example, the prosthesis can be controlled as follows. During the rotation of the forearm stump the receiving sleeve turns, followed by the rotation of the axis of the potentiometer. The potentiometer changes its numerical value. The electronic control unit reads the digital values both from the potentiometer and from the motor driver with feedback set to each motor. Changing the values of the potentiometer leads to a misalignment of the values. The difference in values is the control signal. The electronic control unit sends a control signal to each of the five motor drivers. The direction of rotation of each motor depends on the control signal sent from the electronic control unit. The electronic control unit reads the value of each of the drivers with feedback so that, depending on the operating mode, each value reaches a proportional value with a control signal. As soon as an obstacle is encountered while bending or unbending the finger or the finger has not yet reached the set value, the feedback motor driver gives the signal to the electronic control unit to turn off the motor on the corresponding finger.

Thus, some fingers may stop, while others continue to move towards a given point. Changing the modes of operation is as follows: in the permanent memory, the modes and values for each of the fingers are recorded, by changing the value of the mode, pressing the buttons 12 or 13 of FIG. 3, the feedback controllers are assigned new ranges of values and the control unit works in accordance with the selected mode.

Examples of operating modes are: (a) all fingers bend and unbend simultaneously; (b) the little finger and the annulary are bent, the other fingers bend and unbend simultaneously. The (b) mode can allow the patient to grip small items with the prosthesis.

It will of course be appreciated by those skilled in the art that many variations of the described embodiments would be possible within the scope of the invention defined by the claims herein.

The invention claimed is:

1. A prosthesis for a person with an amputation above the wrist and below the elbow to provide a replacement for the hand and a portion of the lower arm of the person, the prosthesis comprising:
   a receiving sleeve adapted to be attached to the lower arm stump of the person such that the stump can rotate the receiving sleeve;
   a sleeve casing adapted to fit over the stump of the person, the sleeve casing including a back portion and a forward portion, the back portion having a hollow cavity therewithin for receiving the stump;
   an electromechanical hand attached to the receiving sleeve, the electromechanical hand having a rotary mechanism, a control unit, at least one finger and at least one motor;
   wherein the rotary mechanism includes a rotary potentiometer having a shaft in communication with the receiving sleeve such that a rotation of the receiving sleeve causes a corresponding rotation of the shaft of the potentiometer; and
   wherein the control unit is configured to measure the corresponding rotation of the shaft of the potentiometer and send a signal to the at least one motor to actuate the at least one finger.

2. The prosthesis of claim 1, wherein:
   the receiving sleeve is mounted within the hollow cavity of the sleeve casing, and the receiving sleeve is adapted to snuggly fit the stump such that the stump can rotate the receiving sleeve.

3. The prosthesis of claim 2, further comprising a battery pack module removably received within a receptacle in the prosthesis and connected to the control unit or the at least one motor for providing electrical power thereto.

4. The prosthesis of claim 2, further comprising five fingers and a separate motor for each finger.

5. The prosthesis of claim 2, wherein the receiving sleeve is fixed to the shaft of the potentiometer.

6. The prosthesis of claim 2, further comprising a control switch for selecting different modes to capture and hold an object, the control switch being located on an external surface of the electromechanical hand and adapted to configure the control unit.

7. The prosthesis of claim 2, wherein the control switch is adapted to configure minimum and maximum values of the rotation of the receiving sleeve.

8. The prosthesis of claim 2, further comprising an internal memory unit for storing configuration data of the control unit.

9. The prosthesis of claim 1, further comprising a battery pack module removably received within a receptacle in the prosthesis and connected to the control unit or the at least one motor for providing electrical power thereto.

10. The prosthesis of claim 1, further comprising five fingers and a separate motor for each finger.

11. The prosthesis of claim 1, wherein the receiving sleeve is fixed to the shaft of the potentiometer.

12. The prosthesis of claim 1, further comprising a control switch for selecting different modes to capture and hold an object, the control switch being located on an external surface of the electromechanical hand and adapted to configure the control unit.

13. The prosthesis of claim 1, wherein the control switch is adapted to configure minimum and maximum values of the rotation of the receiving sleeve.

14. The prosthesis of claim 1, further comprising an internal memory unit for storing configuration data of the control unit.

* * * * *